(12) United States Patent
Wolman et al.

(10) Patent No.: US 10,744,247 B2
(45) Date of Patent: Aug. 18, 2020

(54) IMPLANTABLE PUMP IMPELLER THERMAL KNOCKDOWN

(71) Applicant: HeartWare, Inc., Miami Lakes, FL (US)

(72) Inventors: Justin Wolman, Aventura, FL (US); Carlos Reyes, Davie, FL (US); Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 308 days.

(21) Appl. No.: 15/719,719

(22) Filed: Sep. 29, 2017

(65) Prior Publication Data

US 2018/0085508 A1    Mar. 29, 2018

Related U.S. Application Data

(60) Provisional application No. 62/401,508, filed on Sep. 29, 2016.

(51) Int. Cl.
*A61M 1/10* (2006.01)
*F04D 29/18* (2006.01)
(Continued)

(52) U.S. Cl.
CPC .......... *A61M 1/1086* (2013.01); *A61M 1/101* (2013.01); *A61M 1/1036* (2014.02);
(Continued)

(58) Field of Classification Search
CPC .......................... F04D 15/0027; F04D 27/001; A61M 1/1086; A61M 2205/70; A61M 2205/3368; A61M 1/1036; H01F 41/22; C21D 1/54
See application file for complete search history.

(56) References Cited

U.S. PATENT DOCUMENTS

| | | | | |
|---|---|---|---|---|
| 4,782,293 | A | * 11/1988 | Steingroever | ........... H01F 13/00 324/205 |
| 8,419,609 | B2 | * 4/2013 | Shambaugh, Jr. | .... A61M 1/101 600/16 |
| 2007/0119246 | A1 | * 5/2007 | Miyakoshi | ............ A61M 1/101 73/168 |

(Continued)

FOREIGN PATENT DOCUMENTS

| | | | | |
|---|---|---|---|---|
| GB | 1067054 | A | * 4/1967 | ............... C22C 5/00 |
| GB | 1067054 | A |   4/1967 | |
| WO | 20160187057 | A1 |   11/2016 | |

OTHER PUBLICATIONS

Trout, Improving the Distribution of Magnetic Properties in Rare Earth-Cobalt Magnets by the use of Selective Thermal Stabilization. IEEE Transactions on Magnetics, vol. MAG-19, No. 5, Sep. 1983. (Year: 1983).*

(Continued)

*Primary Examiner* — Keith D. Hendricks
*Assistant Examiner* — Joshua S Carpenter
(74) *Attorney, Agent, or Firm* — Christopher & Weisberg, P.A.

(57) ABSTRACT

The present invention relates to kits and methods for calibrating a pump through performance of a thermal knockdown process including demagnetization of an impeller of the pump where the impeller is separate from the pump. By heat treating the impeller, a property of magnetic interaction of the pump is reduced in a repeatable manner. A kit includes a pump with impeller, a controller and an oven. The method generally involves an iterative process of testing the pump for a property related to magnetic interaction of the elements of the pump, removing the impeller from the pump, heating the impeller under controlled conditions, then placing the impeller back into the pump to repeat the test performed initially.

5 Claims, 8 Drawing Sheets

(51) Int. Cl.
  *F04D 27/00*  (2006.01)
  *F04D 29/02*  (2006.01)
  *F04D 13/06*  (2006.01)
  *C22C 5/04*  (2006.01)
  *C22F 1/14*  (2006.01)

(52) U.S. Cl.
  CPC .................. *C22C 5/04* (2013.01); *C22F 1/14* (2013.01); *F04D 13/0653* (2013.01); *F04D 27/001* (2013.01); *F04D 29/026* (2013.01); *F04D 29/18* (2013.01); *A61M 2205/3368* (2013.01); *A61M 2205/36* (2013.01); *A61M 2205/70* (2013.01)

(56) References Cited

U.S. PATENT DOCUMENTS

2009/0204205 A1  8/2009  LaRose et al.
2012/0245681 A1  9/2012  Casas et al.

OTHER PUBLICATIONS

Hughes, Thomas A. Measurement and Control Basics (5th Edition)—11.7.1 DC Motors. (pp. 331-332) ISA. (2015) (Year: 2015).*
International Search Report and Written Opinion dated Dec. 18, 2017, for corresponding International Application No. PCT/US2017/054220; International Filing Date: Sep. 29, 2017 consisting of 12-pages.

* cited by examiner

| Pump Details (enter info re: pump here) | |  |
|---|---|---|
| Impeller | | |
| Pump | | |

BEMF Target

| $BEMF_{final}$ | 15.440 | Target final BEMF at a particular RPM and flow rate |
|---|---|---|
| $\Delta$ for $BEMF_{final}$ | 0.020 | Maximum deviation from target BEMF |

Starting Conditions

| $BEMF_{initial}$ | 17.000 | Initial BEMF measured before heat treatment |
|---|---|---|
| $\Delta$ BEMF | 1.56 +- 0.020 | Knockdown required to calibrate pump |

Expected Final Conditions

| $T_F$ (°C) | 75.0 | Estimated temperature for heat treatment to bring BEMF from $BEMF_{initial}$ to $BEMF_{final}$ |
|---|---|---|

Primary Knockdown (T1)

| $T_1$ (°C) | 73.0 | Temperature for first oven cycle |
|---|---|---|
| $BEMF_1$ | 15.700 | BEMF measured after first oven cycle |

Final Tune (T2)

| Temp. (°C) | $BEMF_2$ (Est.) | |
|---|---|---|
| 75 | 15.450 | Estimate of BEMF based on temperature for second oven cycle |
| | | |

*FIG. 6A*

| $\Delta$BEMF | T for heat treatment (°C) |
|---|---|
| $\Delta$0.5 | 66 |
| $\Delta$1.0 | 69 |
| $\Delta$1.5 | 74 |
| $\Delta$2.0 | 81 |

*FIG. 6B*

|  | Time | Temp | Q | Speed | BEMF | Speed | BEMF |
|---|---|---|---|---|---|---|---|
| Visc = 2.58 |  | 25 | 4.0 | 14000 | 18.00 | 18000 | 29.00 |
|  | 20 | 60 | 4.0 | 14000 | 17.88 | 18000 | 28.88 |
|  | 35 | 60 | 4.0 | 14000 | 17.85 | 18000 | 28.80 |
|  | 35 | 65 | 4.0 | 14000 | 17.82 | 18000 | 28.74 |
|  | 35 | 70 | 4.0 | 14000 | 17.74 | 18000 | 28.57 |
|  | 35 | 75 | 4.0 | 14000 | 17.68 | 18000 | 28.48 |
|  | 35 | 80 | 4.0 | 14000 | 17.63 | 18000 | 28.44 |
| Controller Change Viscosity change Visc = 2.62 | 35 | 85 | 4.0 | 14000 | 17.65 | 18000 | 28.50 |
|  | 35 | 90 | 4.0 | 14000 | 17.56 | 18000 | 28.24 |
|  | 35 | 95 | 4.0 | 14000 | 17.48 | 18000 | 28.10 |
|  | 35 |  | 4.0 | 14000 |  | 18000 |  |
|  | 35 |  | 4.0 | 14000 |  | 18000 |  |

IMPLANTABLE PUMP IMPELLER THERMAL KNOCKDOWN

CROSS-REFERENCE TO RELATED APPLICATION

This application is related to and claims priority to U.S. Provisional Patent Application Ser. No. 62/401,508, filed Sep. 29, 2016, entitled IMPLANTABLE PUMP IMPELLER THERMAL KNOCKDOWN, the entirety of which is incorporated herein by reference.

STATEMENT REGARDING FEDERALLY SPONSORED RESEARCH OR DEVELOPMENT n/a

TECHNICAL FIELD

The present invention relates to kits and methods for calibrating implantable blood pumps so that performance characteristics for each pump are the same.

BACKGROUND

Certain magnetic blood pumps include an impeller having a permanent magnetization. For example, the impeller may interact with electrical coils in a stator so that the impeller and stator cooperatively form an electric motor which drives the impeller when alternating currents are applied to the coils in sequence. Implantable blood pump performance is often monitored by a controller connected to the pump. Controllers for monitoring pumps can use control algorithms which determine a parameter based on a magnetic interaction between the impeller and the stator, and use that parameter to monitor the operation of the pump. For example, the interaction between the impeller and coils of the stator, which are momentarily inactive, generates a voltage referred to as "back electromagnetic force" or "back EMF". As discussed in United States Patent Application Publication 2012/0245681, the magnitude of the back EMF in certain axial-flow blood pumps is related to axial force on the impeller, and can be used to estimate blood flow through the pump.

However, when nominally identical pumps are made in serial production, there is considerable variability in the strength of the magnetic interaction between the impeller and stator in different pumps even through the pumps are nominally of identical construction. For example, different pumps in the series will yield different back EMF under identical operating conditions. This arises due to differences in the magnetic strength of the impellers, differences in the properties of the stators, or both. In particular, the magnetic strength of the impellers may vary due to subtle differences in microstructure of the metals constituting the impeller. It is difficult to eliminate these differences in production. One solution to this problem is to measure the back EMF of the various pumps in the series during manufacture and apply a calibration factor to each pump compensate for the variability. However, this does not offer a complete solution. The voltage sensor used to measure the back EMF must be capable of measuring the greatest back EMF generated by the pump with the strongest magnetic interaction, and thus must have a large dynamic range. Such a sensor may not give precise measurements when measuring a smaller back EMF generated by a pump with a weaker magnetic interaction.

SUMMARY

The present invention advantageously provides a method of modifying a property related to a magnetic interaction between an impeller having permanent magnetization and a blood pump including a stator includes heating the impeller until the property reaches a target value.

In another aspect of this embodiment, the method further includes measuring the property of the blood pump prior to heating the impeller and selecting at least one condition of heating the impeller based on the measured property of the pump.

In another aspect of this embodiment, the at least one condition is a temperature used in heating the impeller.

In another aspect of this embodiment, the selecting is conducted using (i) a difference between the measured property of the pump prior to heating the impeller and the target value of the property and (ii) data relating change in the property to treatment temperature compiled from experimental data obtained in previous heating of impellers of one or more blood pumps of the same nominal configuration.

In another aspect of this embodiment, the method further includes separating the impeller from the stator after the measuring and before heating the impeller, and combining the impeller with the stator after the heating.

In another aspect of this embodiment, the method further includes repeating the above steps with the same blood pump, and wherein repeating the above steps includes selecting a second condition for heating the impeller.

In another aspect of this embodiment, the method further includes repeating the above steps with a plurality of different blood pumps.

In another aspect of this embodiment, the measuring includes pumping a test fluid of known viscosity at a fixed test flow rate of fluid and a fixed test impeller speed with the blood pump.

In another aspect of this embodiment, the impeller includes a magnetic alloy selected from the group consisting of platinum-cobalt alloys and platinum-cobalt-boron alloys.

In another aspect of this embodiment, the magnetic alloy is a platinum-cobalt alloy containing about 77% platinum and 23% cobalt.

In another aspect of this embodiment, heating the impeller includes exposing the impeller to a predetermined temperature above ambient temperature until a temperature of the impeller is substantially equal to the predetermined temperature above ambient temperature.

In another aspect of this embodiment, the predetermined temperature is at least 73 degrees Celsius.

In another aspect of this embodiment, the property is back electromotive force.

In another embodiment, a method of modifying at least one blood pump including a stator and an impeller with permanent magnetization includes heating the impeller for a first heating cycle at a first temperature, measuring a property related to magnetic interaction between the impeller and the stator, and if a value of the property related to magnetic interaction after the first heating cycle is greater than a predetermined target value of the property, heating the impeller for a second heating cycle at a second temperature higher than the first temperature.

In another aspect of this embodiment, the property equals the predetermined target value of the property after the second heating cycle.

In another aspect of this embodiment, the first temperature of the first heating cycle is maintained until a temperature of the impeller is substantially equal to the first temperature.

In another aspect of this embodiment, the first temperature is at least 73 degrees Celsius.

In yet another embodiment, a kit for calibrating a pump having a stator and an impeller includes a heater sized and configured to heat treat the impeller. A controller is configured to measure back electromotive force related to a magnetic interaction between the impeller having permanent magnetization and the blood pump including the stator.

In another aspect of this embodiment, the heater is configured to heat treat the impeller based on a comparison of the back electromotive force measured by the controller and a target back electromotive force value.

In another aspect of this embodiment, the impeller is made of a platinum cobalt alloy.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 6A is a table showing an example of how data obtained from testing a magnetic property of the pump is compared with the lookup table to produce temperature values usable for an iterative thermal knockdown process;

FIG. 6B is an example of a lookup table;

DETAILED DESCRIPTION

Figure 1:
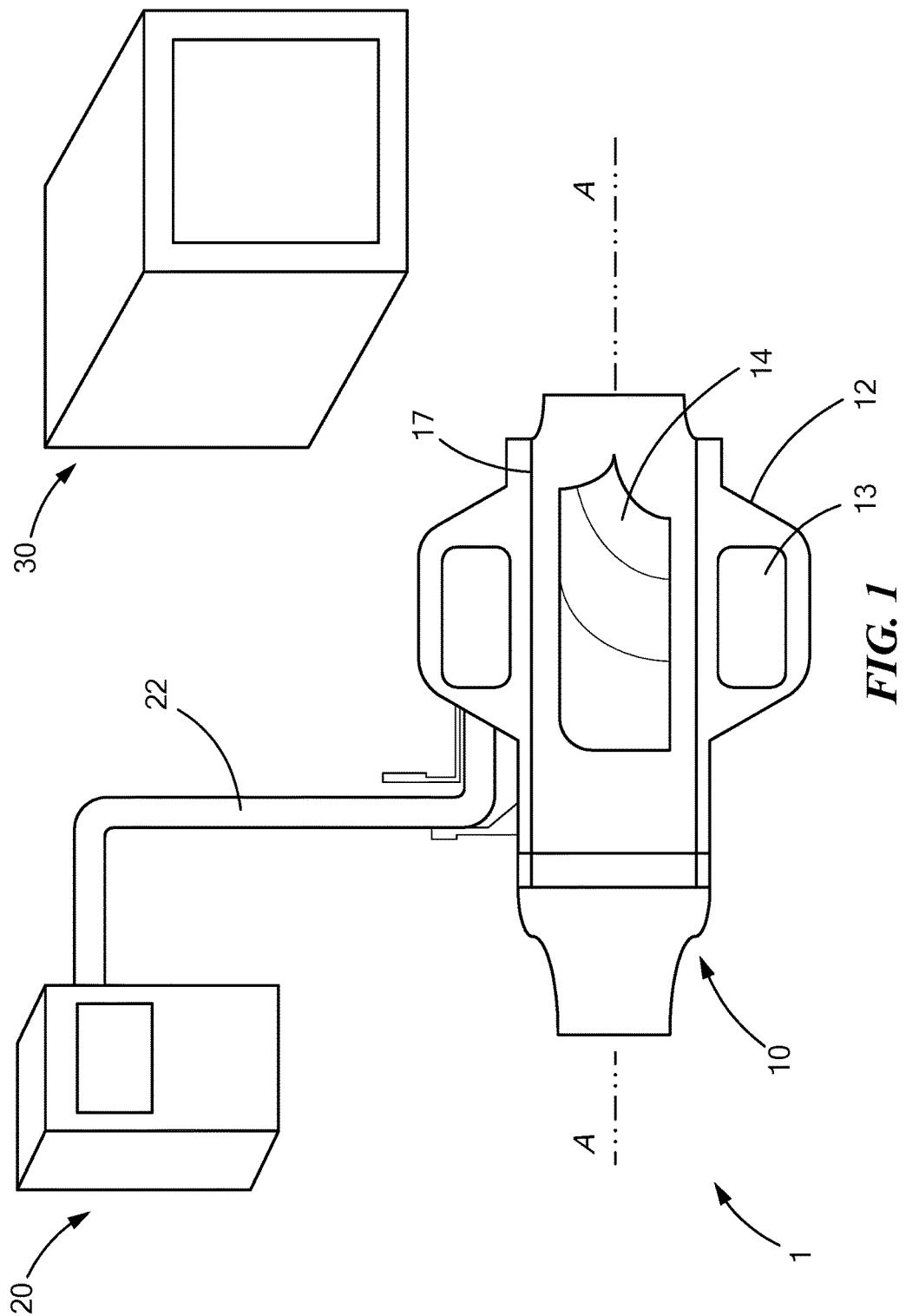
FIG. 1 is a diagrammatic perspective view illustrating a kit in accordance with one embodiment of the invention.

One aspect of the present disclosure addresses the above-mentioned needs. Although the embodiments and examples of the invention are described in the context of blood flow for an implantable pump to assist with the function of the heart, description of the invention in this context is not intended to be limiting in any way.

A kit 1 according to a first embodiment of the invention and shown in FIG. 1 can be used in adjusting the magnetic interactions of pumps, as in the methods discussed below.

The kit includes one or more implantable pumps 10, most typically a plurality of pumps of nominally identical design made in serial production. For clarity of illustration, only one pump is depicted in the drawings. Each pump includes a tubular inner housing 17, and a fixed assembly including a stator 12 surrounding housing 17 and an impeller 14. The stator includes coils 13 on a ferromagnetic frame. In one example, pump 10 is a mini ventricular assist device ("MVAD"), weighing as little as 75 grams and as described in U.S. Pat. Pub. No. 2012/0245681, hereby incorporated by reference herein in its entirety. The impeller is made of a metal or metal alloy and is permanently magnetized. At least the outer surface of the impeller is made of a biocompatible material. For example, the impeller may be a unitary piece of a platinum cobalt alloy. One particular platinum cobalt alloy contemplated contains 77% platinum and 23% cobalt. In another variant, the impeller is made of platinum cobalt boron, such as the impeller described in U.S. Pat. Pub. No. 2009/0204205, hereby incorporated by reference herein in its entirety. The impeller 14 is adapted to rotate and impel blood while disposed in pump 10. Pump 10 is also connectable with a control and measurement device, such as controller 20. Pump 10 is configured so that magnetic fields of stator 12 and impeller 14 can interact. For example, when pump 10 receives power from a power source, such as a battery, coils 13 of stator 12 are driven and a magnetic field forms that is directed transverse to a longitudinal axis of a bore of housing 17. The magnetic field created in stator 12 interacts with a magnetic field of impeller 14, and this causes impeller 14 to rotate. The rotor is suspended within housing 10 by magnetic and hydrodynamic forces, and does not contact the housing during normal operation.

Kit 1 further includes a controller 20 connectable to pump 10, as shown in FIG. 1. Controller 20 includes a driver circuit to power pump 10 and a control circuit with a module to measure a property related to the magnetic interaction between two objects, such as stator 12 and impeller 14 of pump 10. The term "magnetic property" as used throughout this application is intended to refer generally to the property related to the magnetic interaction between the stator and the impeller. One non-limiting type of magnetic property that can be measured by controller 20 is back electromotive force ("BEMF"). Controller 20 can also monitor other parameters of pump 10, such as those described in U.S. Pat. Pub. No. 2012/0245681. In one variant, and as shown in FIG. 1, a cable 22 connects controller 20 to pump 10. The cable can have a cover (not shown) at its end to protect the connection between cable 22 and controller 20. In another variant, pump 10 is configured so that measurements can be transmitted wirelessly to controller 20 without cable 22. The power source for the controller may include a connection to utility power, one or more batteries, or any other source of electrical energy.

Figure 3A:
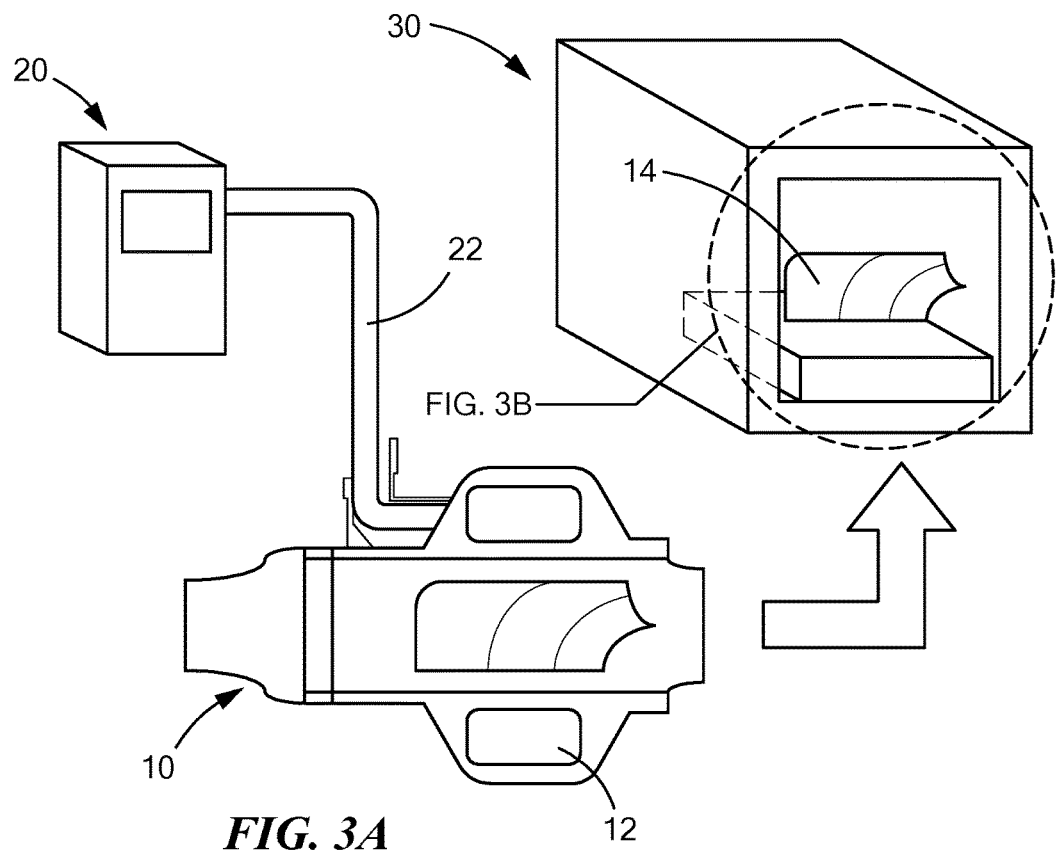
FIG. 3A is a diagrammatic perspective view illustrating another step in the method.
Figure 3B:
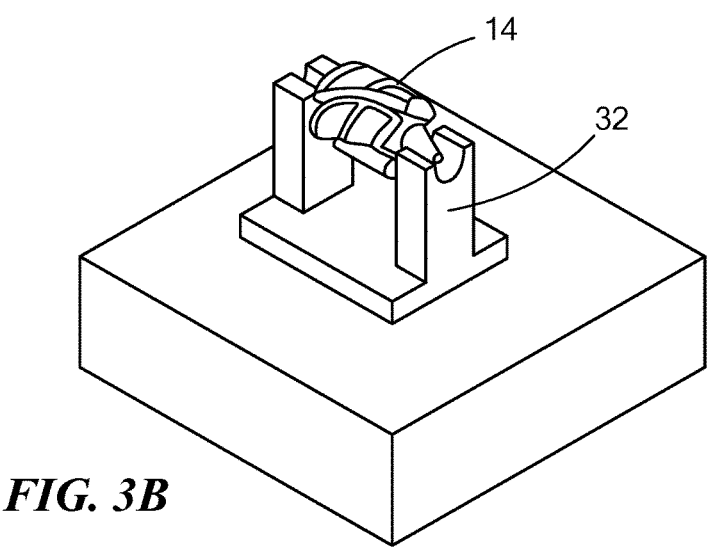
FIG. 3B is a close up diagrammatic perspective view of an oven support fixture for supporting an impeller when the impeller is placed into the oven fixture illustrated in FIG. 3A.

Kit 1 further includes a heater such as oven 30 capable of generating heat in an enclosed space, as shown in FIG. 1. Oven 30 is sized to accommodate at least one impeller 14, but its size optionally may be larger. Oven 30 is configured so that it is operable for at least 30 minutes continuously. It is also configured so that heat may be generated in intervals over a set period. Oven 30 is further configured so that its temperature is adjustable. For example, the oven can be on for 30 minutes during which time the temperature may be adjusted. An upper end of operating temperatures for the oven 30 should be sufficient to at least partially demagnetize each individual impeller. With the platinum-cobalt alloys, a capacity for oven 30 to generate heat up to 200° C. is sufficient in most cases. The temperatures needed for the partial demagnetization typically are below the Curie temperature of the alloy. In some variants, an oven support fixture 32 is included with oven 30. The oven fixture is configured to support impeller 14, as shown in FIG. 3B. Finally, the kit 1 also includes inflow and outflow tubes (not shown) and a tank (not shown). The inflow and outflow tubes are configured to engage with an inlet 15 and outlet 16 of pump 10, respectively. Each tube is further configured to engage with the tank. The tubes include material properties and have geometry so that liquids and flow rates that are contemplated are accommodated. For example, the tubes can support a liquid with a viscosity equal to that of blood, i.e., 2.58 centipoise. The tank is sized and otherwise configured to hold the liquid used for pump testing and to allow outflow and inflow of the liquid.

The kit 1 as discussed above may be pre-assembled and supplied as a unit or in the alternative, each element may be supplied separately and brought together at the point of use.

Figure 2:
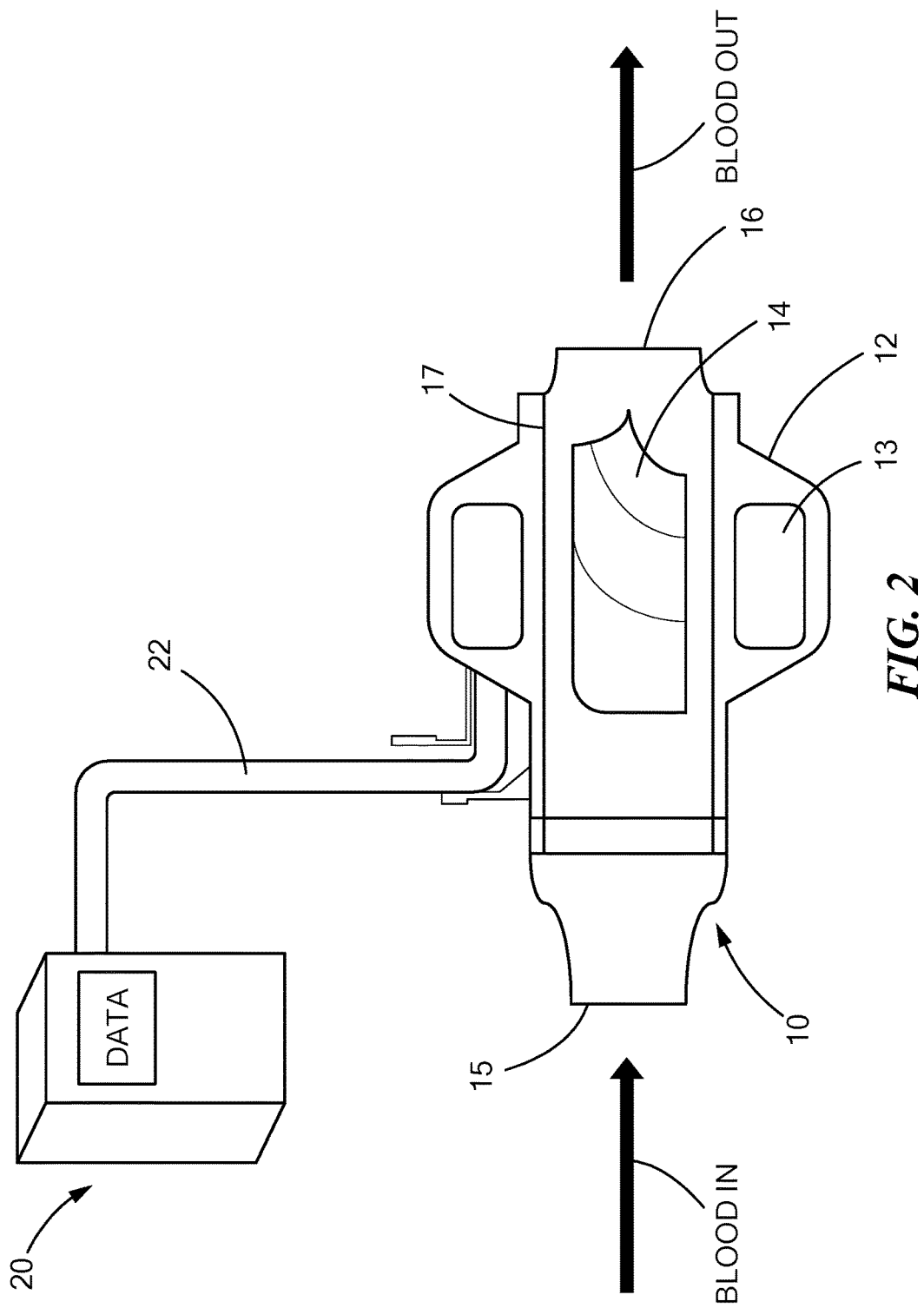
FIG. 2 is a diagrammatic perspective view illustrating an initial step of a method according to one embodiment of the invention, employing components of the kit of FIG. 1.

A method according to a further embodiment of the invention can be practiced using kit 1. At the beginning of the method, each of the pumps is in an assembled condition, with the impeller in inner housing 17 and with stator 12 in place around the outside of housing 17, so that impeller 14 of each pump is disposed inside stator 12. The appearance of the pump as assembled is shown in FIG. 2.

Figure 4:
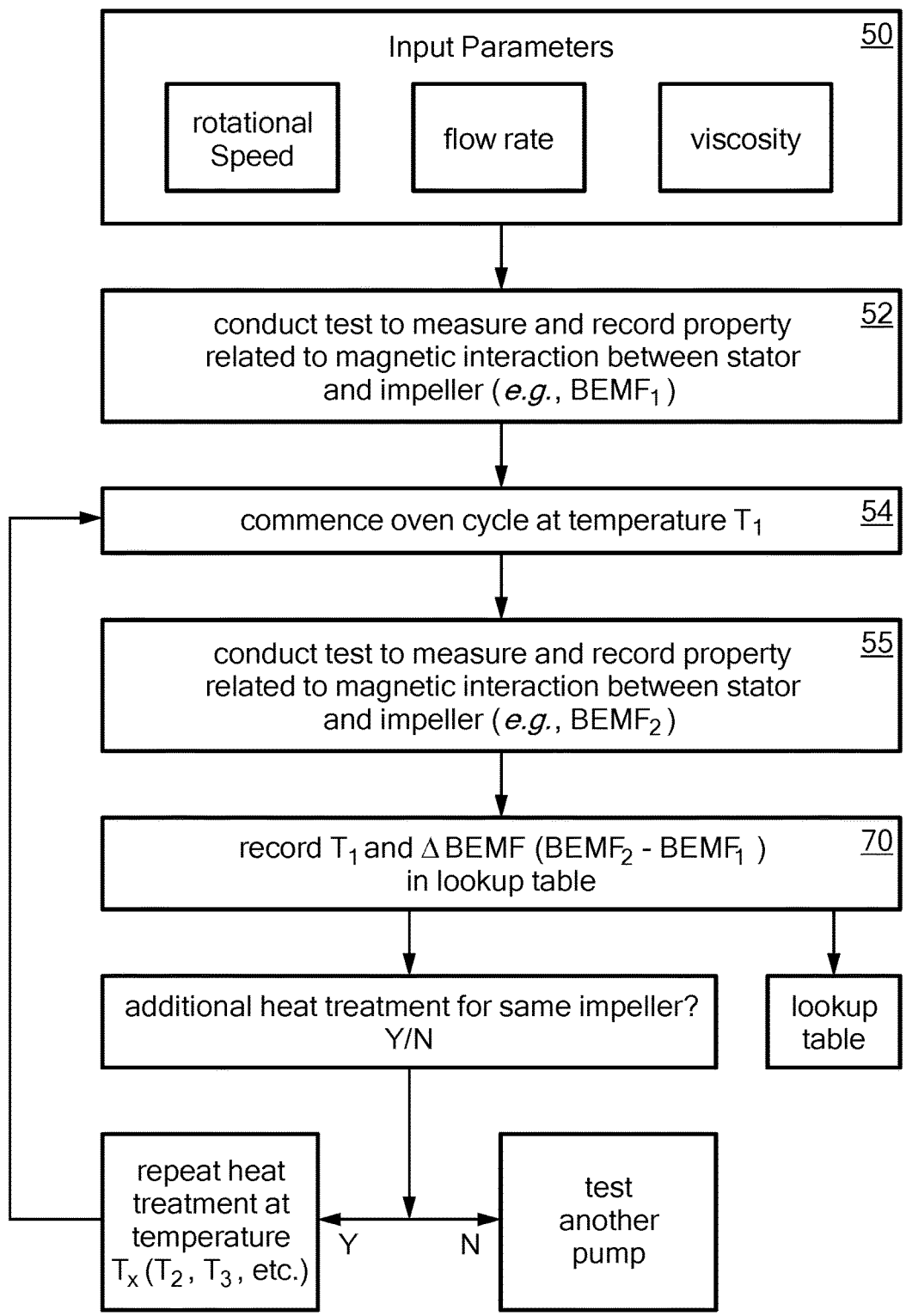
FIG. 4 is a flow chart for further steps of the method shown in FIG. 2 describing how testing is performed to gather experimental data for a lookup table.
Figure 5:
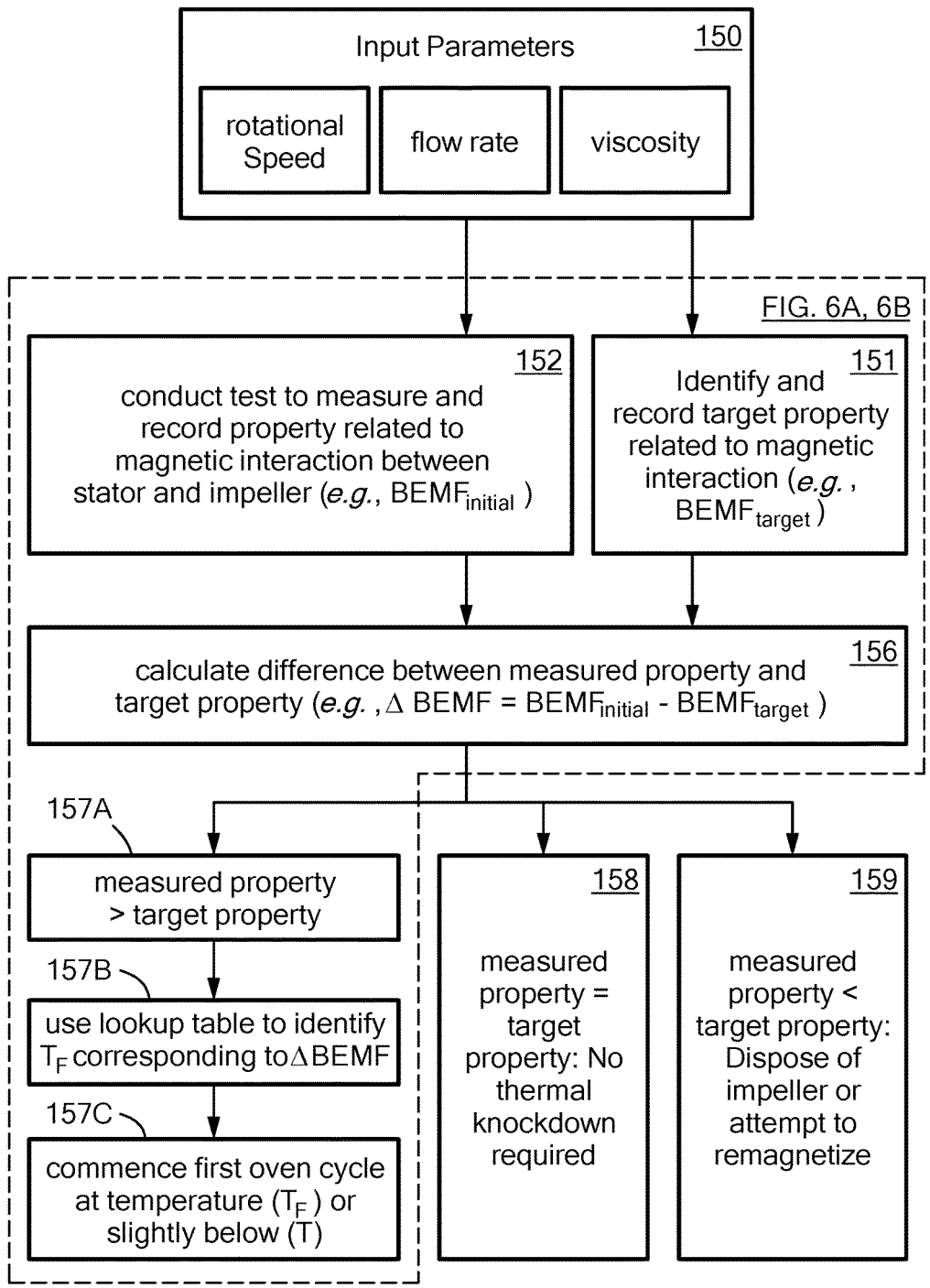
FIG. 5 is a flow chart for further steps of the method shown in FIG. 2 describing how a pump is calibrated through heat treatment of an impeller.

For each pump, the method begins with an initial measurement of a magnetic property of the pump. This is done irrespective of whether the pump is to be tested for experimental data or whether it is to be calibrated. To measure the magnetic property of the pump, each pump, in its assembled condition, is operated to pump a liquid under fixed test conditions 50, 150, and the magnetic property (BEMF) is measured during such operation (FIG. 4). In particular, the pump is connected to inlet and outlet tubes (not shown) at inlet 15 and outlet 16 of pump 10, respectively, as necessary to facilitate the flow of a fluid, such as an aqueous sugar solution having viscosity similar to that of blood, through the pump for testing purposes. Controller 20 is connected to the pump via cable 22, as seen in FIG. 2. As shown in FIGS. 4 and 5, fixed conditions 50, 150 are then input into a computer connected to the controller or an interface of the controller 20. These conditions will be maintained throughout the test to measure the magnetic property of pump 10. In one exemplary test, viscosity of the liquid to be pumped, impeller rotational speed and flow rate are used as inputs for the test of pump 10. In addition, because the pump is intended for use with blood, the viscosity of the liquid is typically 2.78 centipoise, equal to that of blood. In any event, if the viscosity is another amount, it should be in the range of 2.50-2.90 centipoise. Each of these parameters are shown as inputs 50, 150, in the flow chart illustrated in FIGS. 4 and 5. For each pump tested to gather experimental data for the lookup table, and for later pumps calibrated based on the data in the lookup table, the above parameters are used in a consistent manner. For example, the viscosity, pump speed and flow rate used are the same for each pump, both for those used to gather experimental data and those for calibration. When input parameters 50, 150 are confirmed and finalized, the test to determine a magnetic property 52, 152 of the pump may commence. The controller applies power to the stator of the pump, causing magnetic fields of the stator and impeller to interact and the impeller to rotate. Once the pump is operating under the conditions specified by the input parameters, the magnetic property, in this case the BEMF, is measured by a voltage sensor (not shown) incorporated in the controller and electrically connected to a coil of stator 12 during periods when power is not applied to the coil. Once the measurement is obtained, it is recorded 52, 152, as shown in FIGS. 4 and 5.

Prior to calibrating a series of pumps with the same nominal design, experimental data is gathered from a subset of the series of pumps. The experimental data is used to create a lookup table that can be used to determine heat treatment needed to calibrate pumps. Steps to gather experimental data for each pump include initial magnetic property measurement, as described above, disassembly, heat treatment of the impeller, reassembly, and further magnetic property measurements. These steps will now be described in detail. Following measurement of magnetic property 52 of a pump, the impeller is heat treated. To perform heat treatment, impeller 14 is first removed from pump 10, as shown in FIG. 3A. The impeller 14 may be cleaned prior to placing it into oven 30. This also applies for placing impeller 14 back into pump 10 after the heat treatment. Impeller 14 is then placed onto oven support fixture 32, as shown in FIG. 3B. In a variant, other forms of securement or support can be used to hold impeller 14. Oven 30 is turned on and heated to a preselected temperature. Once the oven is heated to the preselected temperature, oven support fixture 32 with impeller 14 disposed thereon is placed inside, as shown in FIG. 3A. The oven is then closed and once the temperature returns to the preselected temperature, heat treatment 54 begins. Provided that the duration of heat treatment 54 is longer than a threshold time, typically about 20-25 minutes, thermal knockdown does not vary significantly with duration. Thus, the heat treatment typically is conducted for a duration longer than the threshold time, typically about 30 minutes or more. The knockdown is repeatable for pumps of a given nominal configuration and impeller composition. Thus, the heat treatment temperature necessary to achieve a given knockdown can be determined based on experimental data derived from prior heat treatments of other pumps of the same nominal design. In some variants, the temperature used for heat treatment of one impeller can be different from others, and, as discussed below, any one impeller can be subject to additional heat treatment at progressively higher temperatures.

Removing the impeller 14 from the pump to perform heat treatment demagnetizes the impeller 14 as heat within the temperature range used in the process will not demagnetize the impeller when the impeller is disposed in a magnetic circuit which may comprise an impeller and a ferromagnetic stator of the pump. Any variability in a stator of a pump is accounted for in this approach because the magnetic property of the pump, i.e., BEMF, is measured with the impeller in the pump, and is a measurement of the interaction between the impeller and stator. Therefore, although only the impeller is heat treated, the level of heat the impeller is subject to is intended to calibrate the pump, not the impeller by itself. Through empirical testing, it was discovered that heat treatment of the impeller alone was an effective means of partially demagnetizing impellers, and in turn, calibrating a series of pumps.

After heat treatment, the impeller is taken out of the oven and is cooled. In one example, the impeller is cooled for approximately 20 minutes. Then, the pump is reassembled (using the same stator and impeller) and re-tested under the same fixed test conditions and the magnetic property is measured again 55 (e.g., $BEMF_2$). As will be described below, additional cycles 72 of heat treatment can be performed on the same impeller as desired. It has been established through experimentation that for a pump of a given nominal design, the BEMF will decrease as a result of heat treatment of the impeller. The magnitude of the decrease (referred to herein as the "knockdown") varies with the temperature used in heat treatment.

For each heat treatment temperature used, the resulting change in magnetic property (such as ΔBEMF, the difference between a BEMF measurement before one or more heat treatments and after) is recorded 70. The ΔBEMF represents the difference between the second test of the magnetic property of the pump and the first test (FIG. 4). The experimental data thus yields data correlating change in magnetic property with heat treatment temperature. In one example, the data will be collected in a lookup table. The lookup table includes two columns: One for desired decrease in a magnetic property (e.g., ΔBEMF) and the other for the elevated temperature for heat treatment that will decrease the magnetic property by ΔBEMF. One example of such a lookup table is shown in FIG. 6B. The experimental data for the lookup table can be based on testing of any number of pumps, for example, two, five or twenty, the data for each pump corresponding to a row on the table. In a variant, the experimental data can be obtained using tests conducted in a stepwise manner 72 (i.e., multiple cycles of heat treatment). For example, a single pump may be subject to an initial magnetic property measurement, followed by heat treatment of the impeller at a first treatment temperature such as 50° C. The pump can be reassembled and the magnetic property measured again to establish the change in magnetic property associated with the first treatment. The same pump can be disassembled, and the impeller can be treated at a second temperature 72 higher than the first. Measurement of the magnetic property after reassembly yields a new value of the magnetic property. Thus, the ΔBEMF in this instance is the difference between the third (last) measurement minus the initial measurement and it corresponds to the second heat treatment temperature. After it is determined that no further heat treatment will be performed for the pump under test, the operator may start the process again with another pump if more test data is desired. To the extent that knockdown varies among pumps subject to the same heat treatment temperature, averages can be calculated to determine values to incorporate into the lookup table. Of course, in a variant, each pump can be heat treated in a single iteration or three, four or more iterations. The goal in gathering experimental data for the lookup table is to ensure it is sufficient as a reference for the calibration of pumps, so the amount of data collected is typically a reflection of that goal.

When sufficient experimental data has been collected for the lookup table, calibration of pumps may commence. The pumps which are calibrated in this step have the same nominal design as the pumps tested to gather the experimental data. To calibrate pumps, a target magnetic property 151 is first identified, as shown in FIG. 5. Target 151 (e.g., $BEMF_{target}$) represents a magnetic property measurement for the pump that corresponds to successful calibration. For the purpose of calibrating one or more pumps 10, a tolerance range is established for the target value of magnetic property 151 so that pumps with magnetic properties within the range will be deemed calibrated. In one example where the magnetic property measured is BEMF, if a target value is 15.44 and an acceptable range for the target is ±0.02, then a pump with a measured BEMF anywhere between 15.42 and 15.46 will be satisfactorily calibrated. For ease of explanation, BEMF values referenced in the examples herein are described as numbers without units. In practice, BEMF can relate to voltage or the rate of change of voltage over time. Units can be physical units or be proportional to the physical units.

Typically, in series production of pumps, the goal is to assure that all pumps have BEMF or other magnetic property within a tolerance band from slightly above a target value to slightly below the target value, such as described in the example above. To assure that the heat treatment does not yield a pump with BEMF below the tolerance band, the process can be conducted stepwise. Details of this procedure are described more fully below.

To calibrate individual pumps, an initial magnetic property (e.g., BEMF) is measured for each, as shown in FIG. 5 and as described above. If ΔBEMF 156 determined based on a difference between $BEMF_{initial}$ 154 and $BEMF_{target}$ 151 is greater than zero 157A, the ΔBEMF is checked against a lookup table 157B that includes a list of ΔBEMF values associated with temperatures. The lookup table is developed through the procedure shown in FIG. 4 and described above, and an example of the lookup table is shown in FIG. 6B. A temperature, $T_F$, "T" as shown in FIG. 6B, is identified from the table as an amount of heat to apply to the impeller to calibrate the pump. $T_F$ represents the expected temperature for heat treatment needed to fully calibrate the pump so that after treatment, the measured BEMF will equal $BEMF_{target}$. To the extent that a ΔBEMF value needed for calibration falls between ΔBEMF values on the lookup table, a corresponding temperature for heat treatment can be found through conventional linear interpolation between data points in the lookup table. Alternatively, interpolation between adjacent data points in the lookup table can be based on a function representing of the experimental data. For example, such a function can be derived via curve-fitting. Thus, a lookup table can be used to calibrate pumps of the same group. Other initial properties of the pump, such as magnetization, may also be considered as part of the method, but are principally used to determine whether the pump should be tested at all and are not typically included as experimental data for the lookup table. Magnetization of the impeller is discussed in greater detail below. Although $T_F$ is described as obtained from a lookup table 157B, it is contemplated that the process can be implemented using a computer with the values of a lookup table stored in memory so that an input of ΔBEMF generates a temperature value.

However, the above steps only apply if ΔBEMF is greater than zero. If ΔBEMF 156 is at or below zero 158, 159, then the calibration procedure for that pump is terminated at this stage. For example, if the magnetic property measured in initial test 152 is 15.46 and the tolerance range of $BEMF_{target}$ is 15.42-15.46, then the magnetic property is within the tolerance range of the target magnetic property 151 and no heat treatment is required 158, as shown in FIG. 5. Similarly, if the initial value of a magnetic property is lower than a target value 159, then demagnetization of the impeller will not improve calibration of the corresponding pump, and in such case, the impeller and pump should be disposed of or the impeller remagnetized.

If the initial magnetic property is measured and it is determined that ΔBEMF is greater than zero 157A, the impeller is removed from the pump. A two-step iterative approach to calibration is then implemented. Although described as a two-step approach here, such an approach is merely illustrative and it is contemplated that a single step or a greater number of steps can also be used to calibrate a pump.

The oven 30 is turned on and heated to a temperature $T_1$ slightly below $T_F$ ($T_1$ being a temperature for a first iteration of heat treatment, also shown as an example in FIG. 6A). As described above, $T_F$ is already determined based on the lookup table. The heat treatment procedure for calibration is the same as for the gathering of experimental data already described, except that the temperature used in heat treatment for calibration is determined by referring to the lookup table. For example, the threshold duration for heating, the cleaning steps, and so on are all the same.

The performance of an initial heat treatment 157C at a temperature $T_1$ below $T_F$ tailors the method so that any variation in the knockdown achieved during the initial heat treatment will not reduce BEMF of the pump to a value below the tolerance range.

Following completion of the first oven cycle, but prior to performing the second oven cycle, impeller 14 is placed back into pump 10 and the pump is tested again. If the resulting BEMF value is within the tolerance range, the pump has been successfully calibrated and no further heat treatment is performed. If the BEMF value measured after the first oven cycle is slightly above the tolerance range, the value measured after the first oven cycle is used to verify $T_2$ for the second oven cycle. For example, if the BEMF value measured after the first oven cycle is greater than that expected after treatment at $T_1$ (i.e., the knockdown is less than expected), this indicates that $T_2$ should be increased to slightly above the originally-determined $T_F$. By contrast, if the first heat treatment step at $T_1$ yielded BEMF at or very close to the value predicted for $T_1$, the temperature for the second oven cycle should be close to $T_F$.

FIG. 6A illustrates one example of how calibration data can appear to an operator for the above described two-step iterative approach to thermal knockdown. In the example, the operator begins by setting input parameters for an initial test of BEMF, $BEMF_{initial}$. Input parameters can include rotational speed, flow rate and viscosity, as shown in FIG. 5 (not shown in FIG. 6A). Based on the nominal properties of the pump and the input parameters, a $BEMF_{target}$ is recorded by the operator. A delta, or tolerance range, is also noted as the range of $BEMF_{final}$ for the pump that will be acceptable for purposes of calibration. In the example, the range of acceptable $BEMF_{final}$ is 15.42 to 15.46. Using the input parameters described above, the pump is then placed into operation and a $BEMF_{initial}$ is determined. With values of $BEMF_{initial}$ and $BEMF_{target}$, the operator can then record a $\Delta BEMF$ as shown in FIG. 6A (e.g., 1.56±0.020). Based on $\Delta BEMF$, the operator refers to the lookup table, in the example, as shown in FIG. 6B, and identifies a temperature, $T_F$, associated with the $\Delta BEMF$. As described above, $T_F$ represents heat treatment of the impeller at a temperature that demagnetizes it sufficiently to bring the BEMF of the pump including impeller to within the tolerance range of $BEMF_{final}$, and thus calibrate the pump. Returning to the example, $BEMF_{initial}$ is 17.000 and $BEMF_{final}$ is 15.440. Based on these values, the lookup table suggests $T_F$ is approximately 75° C. Thus, 75° C. is the temperature for heat treatment expected to be required to demagnetize the impeller sufficiently to calibrate the pump. Based on the same input, the interface also displays values for $T_1$ and $T_2$. These values show a procedure for obtaining a measurement of BEMF equaling $BEMF_{final}$ following two or more oven cycles. Thus, in the example, a two-iteration approach is performed by: (1) heating the impeller at 73° C. ($T_1$) for 30 minutes; (2) placing the impeller back into the pump; (3) measuring $BEMF_1$; and (4) making any adjustment to the temperature for the second oven cycle ($T_2$) based on whether $BEMF_1$ is believed to be closer or further from $BEMF_{final}$ after one oven cycle than expected. In the example, $T_2$, the temperature for the second oven cycle, is set to 75° C., as it is expected that $BEMF_2$ will be 15.450 following the second oven cycle, within the acceptable range of $BEMF_{final}$. The operator should expect that the impeller in this instance will be calibrated following heat treatment at $T_2$. Optionally, each pump calibrated as described above can also be catalogued through recordation of identifying information about the impeller and pump, such as the serial number of each.

Throughout the thermal knockdown process, the operator monitors the BEMF measurement, i.e., $BEMF_1$, $BEMF_2$, and so on. As described above, if at any point during the procedure the measured BEMF is lower than $BEMF_{final}$, no further testing should be performed on the impeller. In such cases, the operator must determine whether to dispose of the impeller or whether to attempt to remagnetize it. Similarly, if the expected final conditions as shown in FIG. 6A result in a final temperature, $T_F$, less than 50° C., 50° C. should be used for heat treatment in lieu of the temperature based on the lookup table. In some variants, the fine tuning step can involve two or more iterations in addition to the first heat treatment. For example, after treatment at $T_1$, heat treatment can be performed at $T_2$ then $T_3$, where calibration is achieved following heat treatment at $T_3$. Alternatively, an operator can manually determine $T_1$, $T_2$ and any further temperature increments based on an estimate in view of the $T_F$ in the lookup table. For example, if $T_F$ is 80° C., then $T_1$ for a first oven cycle can be 74° C., $T_2$ for a second oven cycle can be 78° C., and $T_3$ for a third oven cycle can be 80° C. It is contemplated as within the scope of the invention that the above principles can be applied to an iterative process having any number of steps (e.g., one heat treatment cycle, four heat treatment cycles, etc.).

One advantage of the two-step approach described in the above example is that it prevents over demagnetization. For example, if an impeller is heated to a temperature $T_F$ based on the input of $BEMF_{initial}$, and the BEMF measurement after the oven cycle is complete is lower than the acceptable range for $BEMF_{final}$, then the pump cannot be calibrated unless it is successfully remagnetized. Remagnetization of a pump is a time consuming process and would require repetition of the steps described herein for calibration once the pump is remagnetized. Such a problem is avoided with the iterative process, as it is much less likely that excessive demagnetization will occur if an initial heat treatment temperature is lower than that expected to be necessary for calibration.

In some variants of the method, the magnetic field strength ("magnetic strength") of the impeller can be measured directly prior to any heat treatment or prior to the commencement of the method described herein. In one example, the magnetic strength of the impeller is measured with a gauss meter while the impeller is disassembled from the pump stator. During the experimental data gathering phase, the magnetic strength of each impeller used in this phase is measured before and after heat treatment to determine the reduction in magnetic strength due to heat treatment at the temperature used. This information can be assembled in a magnetic strength lookup table similar to the $\Delta BEMF$ discussed above, but correlating expected reduction in magnetic strength with treatment temperature. In calibration of pumps in production, the initial magnetic strength of the impeller can be recorded along with the initial measurement of the magnetic property such as BEMF. Based on the $\Delta BEMF$ established following an initial test of the pump ($BEMF_{initial}$), the heat treatment temperature $T_F$ required for calibration is selected as discussed above. An estimate of a final magnetic strength of the impeller following calibration (i.e., after heat treatment at $T_F$) is established using the magnetic strength lookup table. An advantage of having an estimate of the final magnetic strength is that the operator can filter out weak impellers prior to completing the thermal knockdown process if the magnetic strength of the impeller is estimated to be too low following the knockdown process. For example, proper function of the pump may require that the impeller have a minimum strength as, for example, 80 gauss (G). In this example, if the initial magnetic strength and initial BEMF establish that a final magnetic strength will be less than 80 G based on heat treatment at temperature, $T_F$, the impeller should be disposed of.

Figures 7A, 7B:
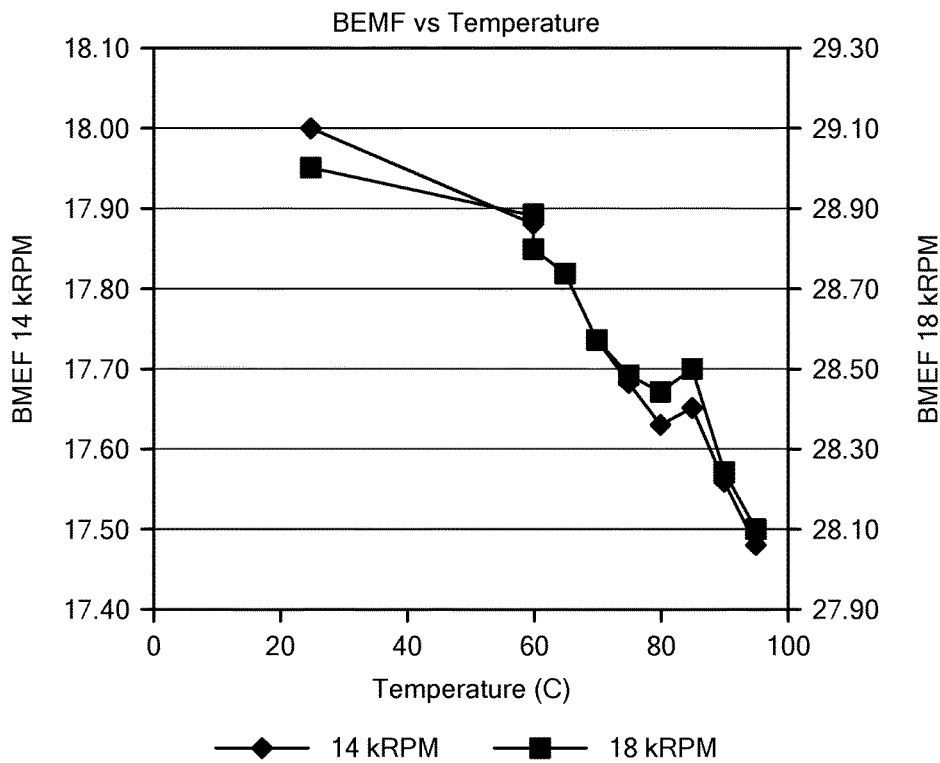
FIG. 7A is a table illustrating empirical data that quantifies the impact of thermal knockdown on back electromotive force measurements.
FIG. 7B is a graph showing the data of FIG. 7A.
Figure 8:
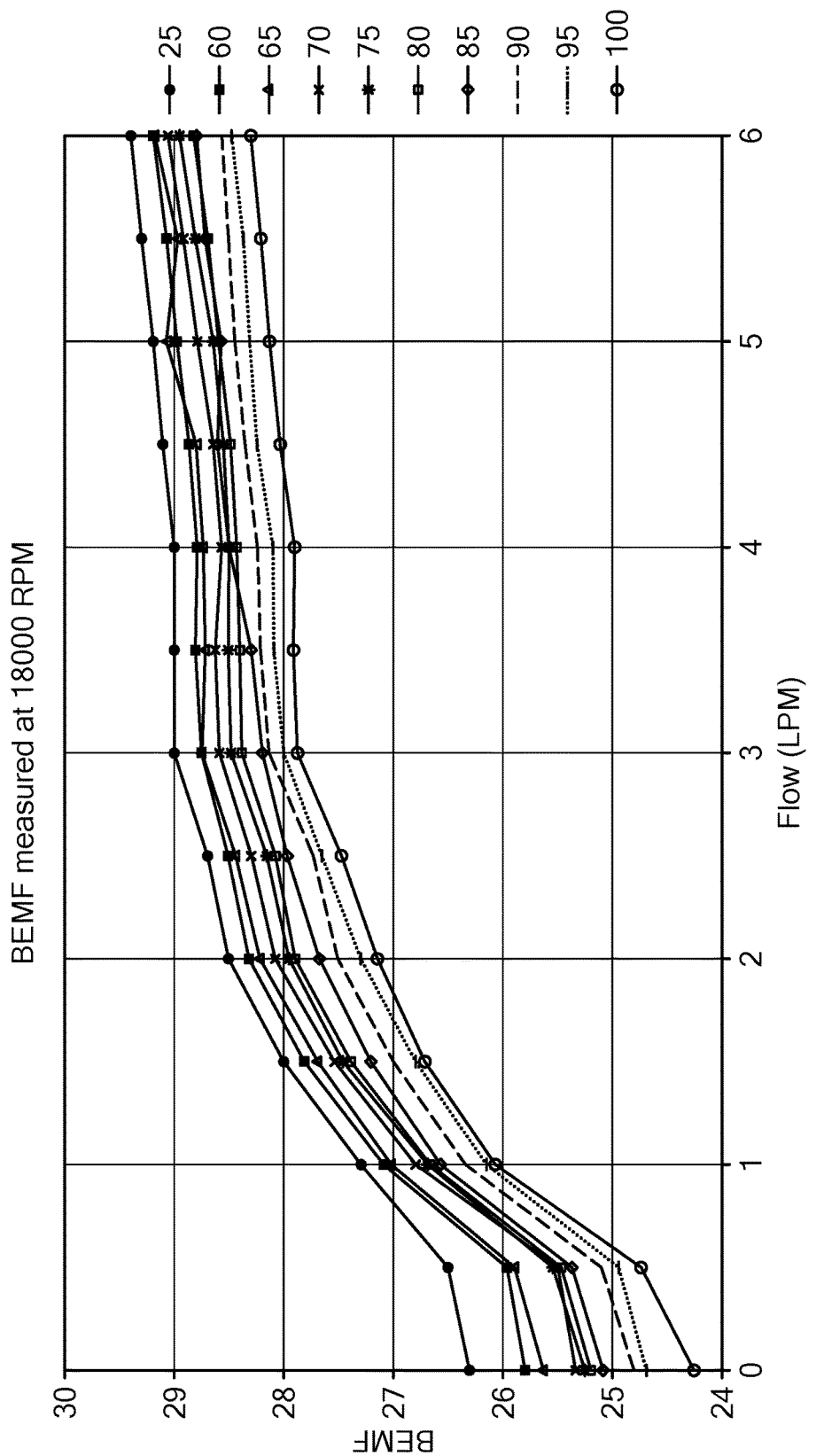
FIG. 8 is a chart illustrating back electromotive force at varying flow rates for impellers subject to different temperature conditions.

Data illustrating the principles of thermal knockdown are shown in FIGS. 7A, 7B and 8. FIGS. 7A and 7B illustrate a set of test data representative of the thermal knockdown effect. In particular, the knockdown effect on a pump is shown over a series of iterations of heat treatment at progressively increasing temperatures. Data is shown for a pump tested at both 14000 RPM and 18000 RPM. As seen in the data, thermal knockdown of an impeller is effective in reducing the BEMF of a corresponding pump when the impeller is placed in the pump. FIG. 8 illustrates the impact of flow rate (an input as described above) during operation of the pump for testing. As seen in the chart, a lower flow rate corresponds to lower BEMF and a lower temperature corresponds to a higher BEMF.

Advantages of the kit and methods described herein include that impellers may be calibrated so that outcomes in terms of magnetic properties are predictable and repeatable. The thermal knockdown methods are also particularly well suited to the MVAD device by Heartware®. Another advantage of the pumps calibrated in the manner discussed is that the stator guards against any changes to the properties of the impeller due to temperature while the impeller is disposed in the housing of the pump. This is due to the ferromagnetic core of the stator, which prevents heat from altering the magnetic properties of the impeller as it would to an isolated impeller separated from the remainder of the pump. For example, if pumps with impellers disposed therein have been calibrated and are being transported or stored under high temperature conditions, such as at 45° C., the stator of each pump will protect the impeller against further changes to its magnetic properties, so it can be expected that the calibrated pumps will continue to possess the properties they had prior to being subject to high temperature conditions.

In the methods discussed above, the magnetic property of the pump is BEMF. Other magnetic properties may be used instead of BEMF. For example, if the pump is equipped with a magnetic sensor such as a Hall Effect device mounted in fixed relationship to the stator, the magnetic property may be the response of the sensor.

The thermal knockdown methods described above can be performed as a sole method of calibration. Thus, because all of the pumps will have substantially the same magnetic properties, they can be used without storing a calibration factor in the control system for each pump. For even greater accuracy, the knockdown method can also be used in conjunction with a calibration factor. For example, a series of pumps can be calibrated using thermal knockdown to lessen the dynamic range among them. The final BEMF measurement taken during calibration can be taken to identify a calibration factor for each pump. This calibration factor can be stored in the control system associated with each pump. Because the dynamic range of the sensors and control circuit is reduced, smaller BEMF measurements may be more accurate than what would otherwise be possible without thermal knockdown.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A method of modifying a back electromotive force related to a magnetic interaction between at least one blood pump including a stator and an impeller with permanent magnetization having a first voltage, comprising:

heating the impeller outside of the at least one blood pump for a first heating cycle at a first treatment temperature between 60 and 95 degrees Celsius until the back electromotive force reaches a second voltage lower than the first voltage;

measuring a back electromotive force voltage related to magnetic interaction between the impeller and the stator; and if the second voltage of the back electromotive force related to magnetic interaction after the first heating cycle is greater than a predetermined target voltage of the back electromotive force, heating the impeller for a second heating cycle at a second treatment temperature between 60 and 95 degrees Celsius that is higher than the first treatment temperature.

2. The method of claim 1, wherein the second voltage of the back electromotive force equals the predetermined target voltage after the second heating cycle.

3. The method of claim 1, wherein the first treatment temperature of the first heating cycle is maintained until a temperature of the impeller is substantially equal to the first treatment temperature.

4. The method of claim 1, wherein the first treatment temperature is at least 73 degrees Celsius.

5. The method of claim 1, wherein the second treatment temperature is approximately 75 degrees Celsius.

* * * * *